United States Patent
Maniglia et al.

[11] Patent Number: 6,161,046
[45] Date of Patent: Dec. 12, 2000

[54] TOTALLY IMPLANTABLE COCHLEAR IMPLANT FOR IMPROVEMENT OF PARTIAL AND TOTAL SENSORINEURAL HEARING LOSS

[76] Inventors: Anthony J. Maniglia, 1 Bratenahl Pl. Suite 1201, Bratenahl, Ohio 44108; Wen H. Ko, 1356 Forest Hills Blvd., Clevelamd Heights, Ohio 44118

[21] Appl. No.: 09/243,508

[22] Filed: Feb. 1, 1999

Related U.S. Application Data

[60] Continuation-in-part of application No. 08/912,710, Aug. 18, 1997, Pat. No. 5,906,635, which is a division of application No. 08/629,540, Apr. 9, 1996, abandoned.

[51] Int. Cl.⁷ .................................................. H04R 25/00
[52] U.S. Cl. .............................................................. 607/57
[58] Field of Search ........................... 607/55, 57; 600/25

[56] References Cited

U.S. PATENT DOCUMENTS 5,277,694  1/1994  Leysieffer et al. ........................ 600/25
5,772,575  6/1998  Lesinski et al. ........................... 600/25

*Primary Examiner*—Scott M. Getzow
*Attorney, Agent, or Firm*—Vytas R. Matas

[57] ABSTRACT

An implantable hearing device for improvement of extreme partial and total hearing loss has a transducer mounted to the malleus of the ossicular chain by METABOND adhesive. The device responds to auditory vibrations of the malleus to establish an electrical signal in response thereto. For total hearing loss restoration, a speech processing unit is mounted inside the mastoid cavity having a intracochlear electrode which is inserted into the cochlea through the oval window to reach the nerve endings thereof and transmit speech signals capable of being understood by the brain. For total hearing loss a totally implantable system with a rechargeable battery, receiving antenna for remote control of on/off switch, volume, speech processor and programing is used with a biologic-electronic microphone activated by the implanted rechargeable battery to interact with implanted electronics for transmission of electrical signals from the transducer directly to the cochlear nerve endings.

9 Claims, 7 Drawing Sheets

Optical Transducer

TOTALLY IMPLANTABLE COCHLEAR IMPLANT FOR IMPROVEMENT OF PARTIAL AND TOTAL SENSORINEURAL HEARING LOSS

CROSS-REFERENCE TO RELATED APPLICATIONS

This is a continuation-in-part of U.S. application No. 08/912,710 filed Aug. 18, 1997, now Pat. No. 5,906,635, which is a Divisional of U.S. Pat. No. 08/629,540 filed Apr. 9, 1996, now abandoned.

BACKGROUND OF THE INVENTION

1. Field of the Invention

The present invention relates to totally implantable hearing devices generally and particularly to totally implantable cochlear implants which stimulate the ossicular chain of the middle ear for restoring partial hearing loss and for totally implantable devices which stimulate the cochlear nerve endings to restore total hearing loss.

2. Description of the Prior Art

Conventional prior art hearing aids are composed of a microphone, an amplifier, a battery as a power source, and a speaker or earphone (commonly referred to as a receiver in the hearing aid industry). Known implantable hearing device have the same basic components, except that the speaker is replaced by a driving vibrating component, such as an electromagnetic coil or a piezoelectric system of biomorph design. Environmental sound energy, as it passes through either device, is converted by the microphone into an electrical signal which is routed to an amplifier. In the conventional hearing aid, the speaker converts the amplified electrical signals into acoustic energy, which is then transmitted to the tympanic membrane and ossicular the speaker is eliminated, being replaced by the vibratory component which drives the ossicular chain.

Partially implantable middle ear hearing devices are also known. These devices have a small, lightweight high coercivity magnet effectively glued to the ossicular chain by a bio compatible bonding material such as METABOND or SUPERBOND adhesives manufactured in the USA and Japan respectively. The magnet is driven by an air core electromagnetic coil optimally spaced from the target magnet at a distance of approximately 1 mm. There is no contact between the air core coil and the target magnet.

These devices have an external unit and an internal unit. The external unit receives, amplifies, and transmits sound energy as radio frequency signals. The external unit consists of a microphone, a radio frequency (RF) amplifier, a transmitting antenna, and a battery. Using existing microchip technology, these components are miniaturized to a unit with dimensions of 10×10×5 mm without the battery.

The internal unit consists of a receiving antenna, a titanium support, implanted electronics, an electromagnetic (EM) transducer (driving coil), and the high coercivity magnet. The electronics (diode and capacitor), driving coil, and magnet are hermetically sealed in a helium filled laser-welded titanium case. A glass-insulated feed-through attaches the electronics to silicone or polytetrafluoroethylene-coated platinum iridium or stainless steel wires of the receiving antenna. The precise alignment of the transmitting (external) and receiving (internal) antennae permits transcutaneous transfer of the sigma delta modulated radio frequency signal (8 to 10 $_{MHZ}$). The implanted electronics function to receive the radio frequency signal that has been processed by the external electronics and to transform this energy into an audio frequency input to the driving coil. The driving coil in turn creates a magnetic field, which activates the target magnet attached to the body of the incus. Through the ossicular chain, the vibrations are transmitted to the inner ear fluids, activating the organ of Corti.

The magnet used is a neodymium-iron-boron (NdFeB) permanent magnet of great coercive force and high flux density. The magnet, weighs 8.0 mg, is hermetically sealed in a laser-welded 6-mg titanium case containing a helium atmosphere. Two of such magnets are used, stacked on top of each other. On the basis of fresh human cadaver studies, the magnet-titanium assembly weight load of 65 mg and 110 mg has a negligible effect at the malleus and incus, respectively, on the frequency response.

The external electronics associated with the transducer are designed to apply only push forces on the magnet-incus assembly. An air-core coil placed in the attic of the middle ear is used because it does not exert a constant bias force on the ossicular chain. If the system is idling, there is no steady force applied to the incus-magnet assembly. In order to determine the size of the driving coil, 20 preserved human cadaver temporal bones were microsurgically dissected. Measurements were made of the mastoid cavity, antrum, attic, and body of the incus. Owing to the anatomic characteristics of the attic, the outside diameter of the driving coil assembled in a titanium case was limited to 5.0 to 6.0 mm. outside diameter. Initially, an efficient coil was built with a 3.0-mm outside diameter, 0.75-mm inside diameter, and a length of 1.0 mm, composed of 2200 turns of 52 AWG copper wire with 600 ohms resistance. A more efficient coil with 2668 turns of 52 AWG copper shire with 875 ohms resistant was later built for short-and long-term animal experimentation. Computer simulations were instrumental in the selection of this coil design. For the human device a coil with 3800 turns and a resistance of 1415 ohms is preferably used. This coil has been tested experimentally and found to generate 76% more force when compared to the 2668 turn coil.

These described devices while operating to provide restoration of partial hearing loss did not have any means to activate the cochlear nerve endings in patients who had total hearing loss due to a malfunctioning cochlea. Also, these devices had no provision for adjusting the device to accommodate growth of the patient over the years which is a problem especially prevalent in implants for growing children. Further, these devices were sensitive to magnetic resonance imaging (MRI)interference and any patient with such devices when subjected to an MRI came out of the scan with an inactive hearing device.

BRIEF SUMMARY OF THE INVENTION

The present invention solves the problems associated with the mentioned prior art devices as well as other problems by providing a substitute transducer for a partially implantable hearing restoration device for partial and total hearing loss improvement. These transducers will be used for the bioelectronic microphone. The ear drum is the diaphragm which vibrates in response to acoustic energy in the external ear canal. It is to be used for the totally implantable cochlear ear implant. The sensor is mounted on the head of the malleus. Vibration of the ear drum—malleus activates the sensor. The mechanical energy is transformed into electrical energy and is amplified by known amplifier chips.

One embodiment used to accomplish this is a dual coil transducer having a hermetically encased copper coil and associated electronics which resonates at a set frequency and a second coil spaced therefrom which is encased in a case and which is bonded to the malleus. The second coil is a titanium coil and capacitor tuned to the operating frequency. The twocoil system detects the vibration of the malleus and establishes an electrical signal in response thereto. A second transducer embodiment uses a piezoelectic transducer (PZT) mounted inside a titanium case which is bonded to the malleus and which establishes electrical signals in response to the vibration of the malleus. A third transducer embodiment uses a capacitive or piezoresistive accelerometer mounted inside a titanium case bonded to the malleus which reacts to the vibration of the malleus to establish an electrical signal in response thereto. A fourth transducer embodiment is based on light reflection. A light emitting diode or laser diode emits light which is reflected by a titanium plate mounted on the head of the malleus to a receiver. The vibrations of the eardrum—malleus causes the receiver to receive light signals of varying strenght which the detector converts to electrical signals. These signals are then amplified by known amplifier chips to provide a usable electrical signal.

In cases of a profound partial or total hearing loss, a programing and speech processor are mounted inside the cavity of the drilled out mastoid bone which are responsive to the electrical signals of the above embodiments responding to the actuations of the ossicular chain to establish signals along an intracochlear electrode located in the cochlea near the nerve endings thereof which are intelligible to the brain when they are transmitted to the brain by these nerve endings. The transducer, amplifiers, speech and programing processor are powered by a lithium ion battery which is sealed in a titanium case and is subcutaneously located to be recharged by radio frequencies.

In view of the foregoing it will be seen that one aspect of the present invention is to provide an implantable hearing device which is insensitive to MRI interference.

Another aspect of the present invention is to provide a totally implantable cochlear implant to improve hearing due to a non functioning cochlea which device is insensitive to MRI interference.

These and other aspects of the present invention will be more fully understood after reviewing the following description of the preferred embodiment when considered with the appended drawings.

DETAILED DESCRIPTION OF THE PREFERRED EMBODIMENT

Figure 1:
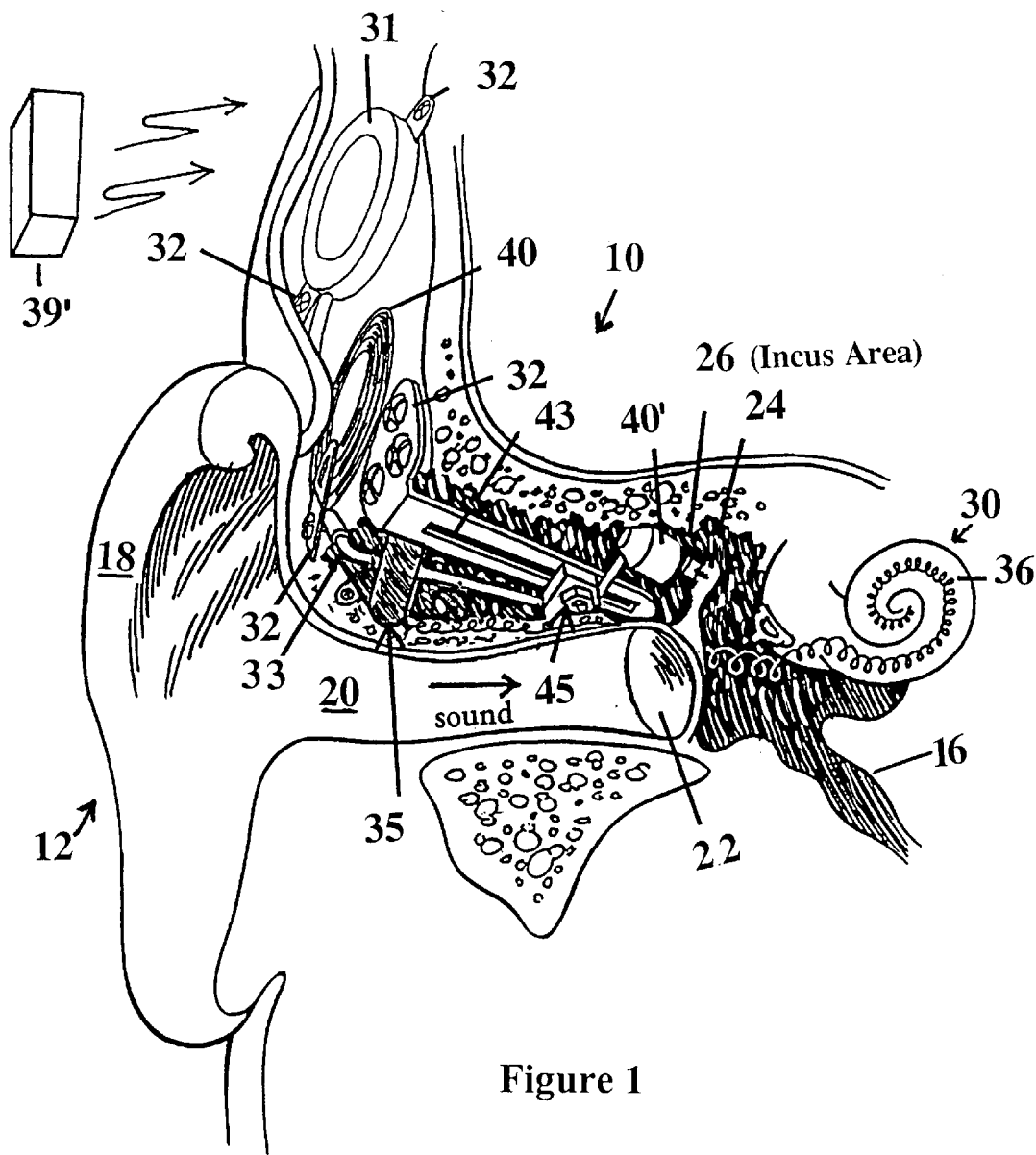
FIG. 1 is a depiction of a human ear having the totally implantable cochlear implant unit of the present invention shown mounted therein for restoration of profound partial or total hearing loss in adult patients and children. This unit as pictured shows the double coil used as the transducer.

Referring now to the drawings generally, wherein like numerals designate the same element throughout the several drawings, there are shown cross-sectional views of an ear, generally referred to as 10. The ear 10 is made up of an outer ear 12, a middle ear 14, and an inner ear 16. The outer ear 12 includes an auricle or pinna 18, and an outer ear canal 20. The pinna 18 collects acoustic energy or sound waves from the environment and directs them into the outer ear canal 20 which conveys the sound waves by air conduction to a tympanic membrane or ear drum 22, which separates the outer ear 12 from the middle ear 14.

The middle ear 14 contains a series of three tiny interconnected bones; the malleus (hammer) 24; the incus (anvil) 26; and the stapes (stirrup). Collectively, these three bones are known as the ossicles of the ossicular chain. The malleus 24 is attached to the tympanic membrane 22 while the stapes, the last bone in the ossicular chain, is attached to the oval window of the inner ear (not shown).

Sound waves that travel down the outer ear canal 20, strike the tympanic membrane 22 and cause it to vibrate. The malleus 24, being connected to the tympanic membrane 22, is thus also set into motion, along with the incus 26 and the stapes. These three bones in the ossicular chain act as a set of levers to amplify the tiny vibrations received by the tympanic membrane 22. By the time the vibrations are transmitted to the oval window (not shown) the pressure vibration, received by the tympanic membrane 22 have been magnified by as much as 22 times. The stapes vibrates in turn, causing fluid in a spiral structure known as the cochlea 30 to move along its length. Very small hairlike cells or nerve endings (not shown) in the cochlea 30 are stimulated by the movement of fluid in the cochlea 30. There, hydraulic pressure displaces the inner ear fluid and mechanical energy in the hair cells is transformed into electrical impulses which are transmitted to neural pathways and the hearing center of the brain (temporal lobe), resulting in the perception of sound. If the cochlea is totally or severely damaged this normal physiology described previously does not occur.

Figure 2:
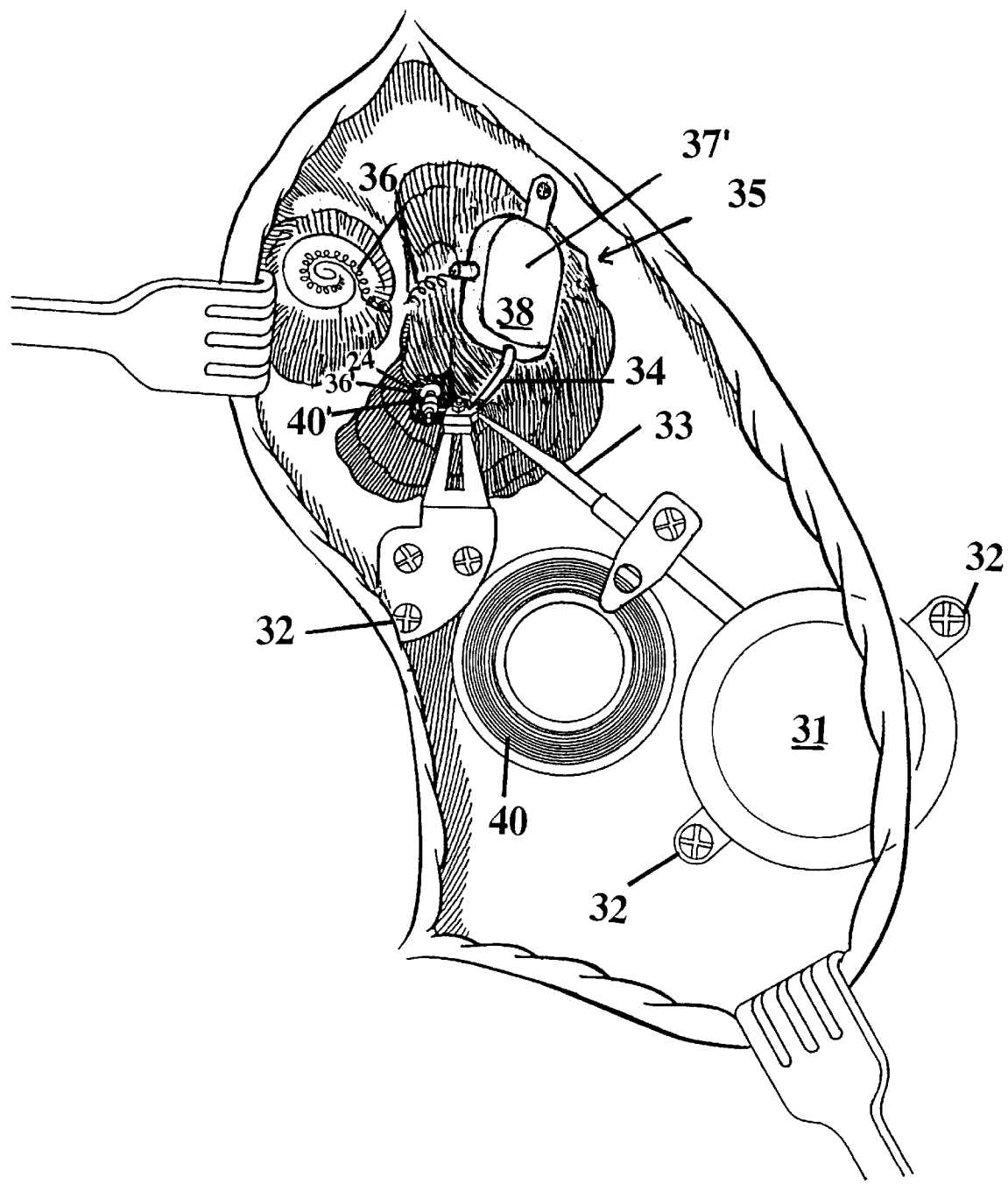
FIG. 2 is an expanded view of the support means and receiving antenna of the FIG. 1 depiction showing components in the mastoid cavity.
Figure 3:
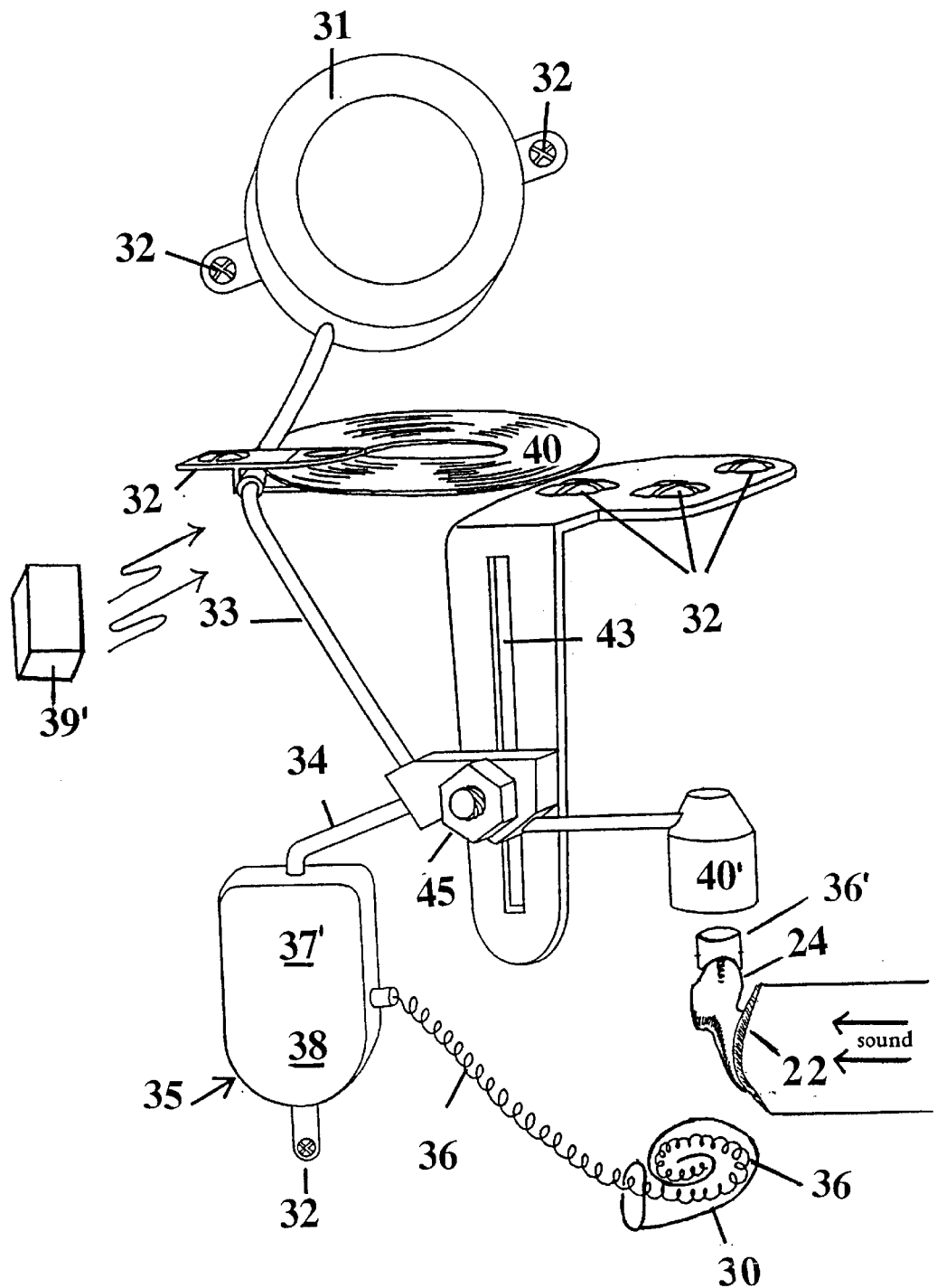
FIG. 3 is an expanded view of the support means and receiving antenna and other of the totally implantable cochlear implant with a double coil transducer mounted on the head of the malleus as shown in FIG. 1.

Turning next to FIGS. 2–3, a device for restoration of profound partial or total hearing loss will be described for patients who are candidates for cochlear implant. Total hearing loss is due to the cochlea 30 of the inner ear being unable to transmit sound energy to the nerve endings therein which then in turn send sound and speech signals to the brain. The partial hearing loss restoration devices described previously are modified as follows to provide a total hearing loss restoration device. Otherwise, the operation and structure thereof remains as described earlier. A battery 31 such as a hermetically sealed rechargeable pacemaker battery is subcutaneously mounted by screws extending through tabs 32 in a known manner. The battery 31 is electrically connected to the titanium tube 33 through a connecting tube 34 of similar construction to power a speech processing and volume control circuit assembly 35 located in the mastoid cavity of the ear. The assembly 35 is hermetically sealed with biocompatible ceramic material and electrically connected to receive electrical signals therefrom along connecting tube 34. The assembly 35 has an intracochlear glass insulated feedtrhough connecting electrode 36 extending therefrom into the cochlea 30 through the round window of the cochlea to activate the nerve endings of the cochlea.

The operation of this device is as follows. The ossicular chain transmits sound and speech signals from the vibration of eardrum 22 which are transmitted by the mentioned transducers and electrical signals are established. These signals are amplified and sent to the speech processing chips and volume control assembly 35 where they are translated into signals which can be processed by the brain. These signals are sent along the intracochlear electrode 36 to the nerve endings of the cochlea 30 to be transmitted by them to the brain.

The titanium or ceramic encased, hermetically sealed assembly 35 is comprised of an on/off and volume control 37' which operates a speech processing assembly 38 for these mentioned functions in response to signals from an externally carried remote control 39' activated by the patient. The speech processor electronics are hermetically sealed in a titanium can and are located surgically in the mastoid cavity. An implanted antenna is used by radio frequency to to turn the device on and off and for volume control and programming of electrodes. The signal is picked up by antenna 40 and demodulated into audio frequency (AF) by implanted diode and capacitor in case 40'. The speech processor 35 and control 39' is readily known from NUCLEUS CORPORATION of Melbourne Australia. Also Clarion Corporation USA and others have similar speech processors which can be miniaturized into microchips. The eardrum and malleus magnet assembly and electromagnetic coil act as a microphone in a reverse cycle as compared with device described for partial hearing loss. Other transducers cited previously (double coil, PZT, accelerometer, and optical) are the alternatives because of their advantage that they are immune to MRI interference. The amplified electric signal reaches the speech processor which activates the cochlear electrode. In cases of total hearing loss this implant technology has no external unit except for the remote control. The implant unit is totally concealed under scalp and skin harboring in the mastoid middle and inner ear. The battery (implanted, rechargeable) with its wire connections provides the necessary power for operation of the different implanted components.

A first embodiment of the present invention is drawn to an external unit, which will be described later, and an internal implantable hearing device generally referred to as internal unit or assembly 32'. The internal assembly 32' includes an implanted unit having a titanium dish assembly 36' shown bonded to the malleus 24 of the ossicular chain. FIG. 3 shows the mounting on the incus which is an alternative mounting. The incus can be removed and mounting of the transducer is then placed on the head of the malleus. Our labrotory tests showed this to be more effective than the incus mounting. A titanium supporting structure having a horizontal support which is screwed into the temporal bone by three screws from which a vertical strip extends at a right angle. The vertical strip has a cut out portion formed therein along which a lock assembly is moved and locked in place to position a Titanium canned copper driving coil with or without a ferrite core and associated electronics 40 spaced approximately 0.5 to 1 mm. away from the dish assembly 36'.

It will be noted that the copper coil may not contain a ferrite core to prevent damaging the unit during any MRI scanning of the individual wearing the unit. The electronics and copper driving coil are all hermetical sealed in laser-welded titanium/ceramic case. A glass-insulated Platinum feed-through post attaches by laser welding the electronics to a silicon or polytetrafluoroethylene-coated platinum iridium or stainless steel wires of the receiving antenna 40. The implanted electronics function to receive the radio frequency signal that has been processed by the external electronics and to transform this energy into an audio frequency field as input to the driving coil. The driving coil with or without a ferrite core in turn creates an electric field, which activates the titanium coil attached to the head of the malleus 24. Through the ossicular chain, the vibrations are transmitted to the inner ear fluids, activating the organ of Corti.

The dish 36' is enclosed in a titanium/ceramic case and can be cemented to the malleus with a post introduced in a hole created by a KTP laser or cemented on the malleus body after light etching of the bone (titanium case with no post). A combination of both methods is feasible. As was mentioned, the easiest, most efficient, and non invasive way is just to cement it to the body of the malleus. The diameter of the encapsulated dish 36' is about the same size as the width of the malleus.

An efficient, biocompatible, adhesive type of cement was the best way to affix the titanium encased transducer on the head of the malleus. There being no such adhesive available for otologic use, we turned my attention to the dentistry literature in order to select a suitable cement that would satisfy our needs. A titanium-bone cement (METABOND) was found to properly secure the magnet to the malleus. METABOND is the USA brand name for an adhesive of multiple compounds developed in Japan by Sun Medical Co. of Kyoto Japan where it is known as SUPERBOND. This adhesive is approved by the U.S. Food and Drug Administration (FDA) as a Class II dental device, #K900303, for cementing titanium to dentine; it has been subjected to previous bio compatibility studies applicable to dentistry. Further research was then done by us to test :he tensile strength and resistance to shearing force and torque, using the rabbit as the animal model. Titanium disks were cemented with METABOND on the tibia of the rabbits after the tibia was etched with citric acid. Experiments in the rabbit after 3 months of implantation have shown excellent results. Our conclusion was that METABOND was most effective and least invasive for binding titanium to bone. The results of chronic experiments in cats demonstrated that METABOND would provide a very effective and long-lasting method of cementing the titanium case 36' to the malleus after it was etched with citric acid. The average survival rate of these animals was 9.6 months. Thus we decided to cement the Titanium housing of the dish 36 and the peg 37 to the head of the malleus by METABOND.

The dish 36' contains a Titanium coil and a capacitor. In operation, sound vibrations are transmitted to the ear drum 22 and therefrom to the malleus. The dish 36' containing the Titanium coil and capacitor resonates at a design frequency activated by the driving coil of the assembly 40'. The driving coil and the electronic circuitry detect the malleus vibration and makes the conversion into an electrical signal. The implantable rechargeable battery powers the dish 36' and the assembly 40 by known wiring (not shown).

Figure 4:
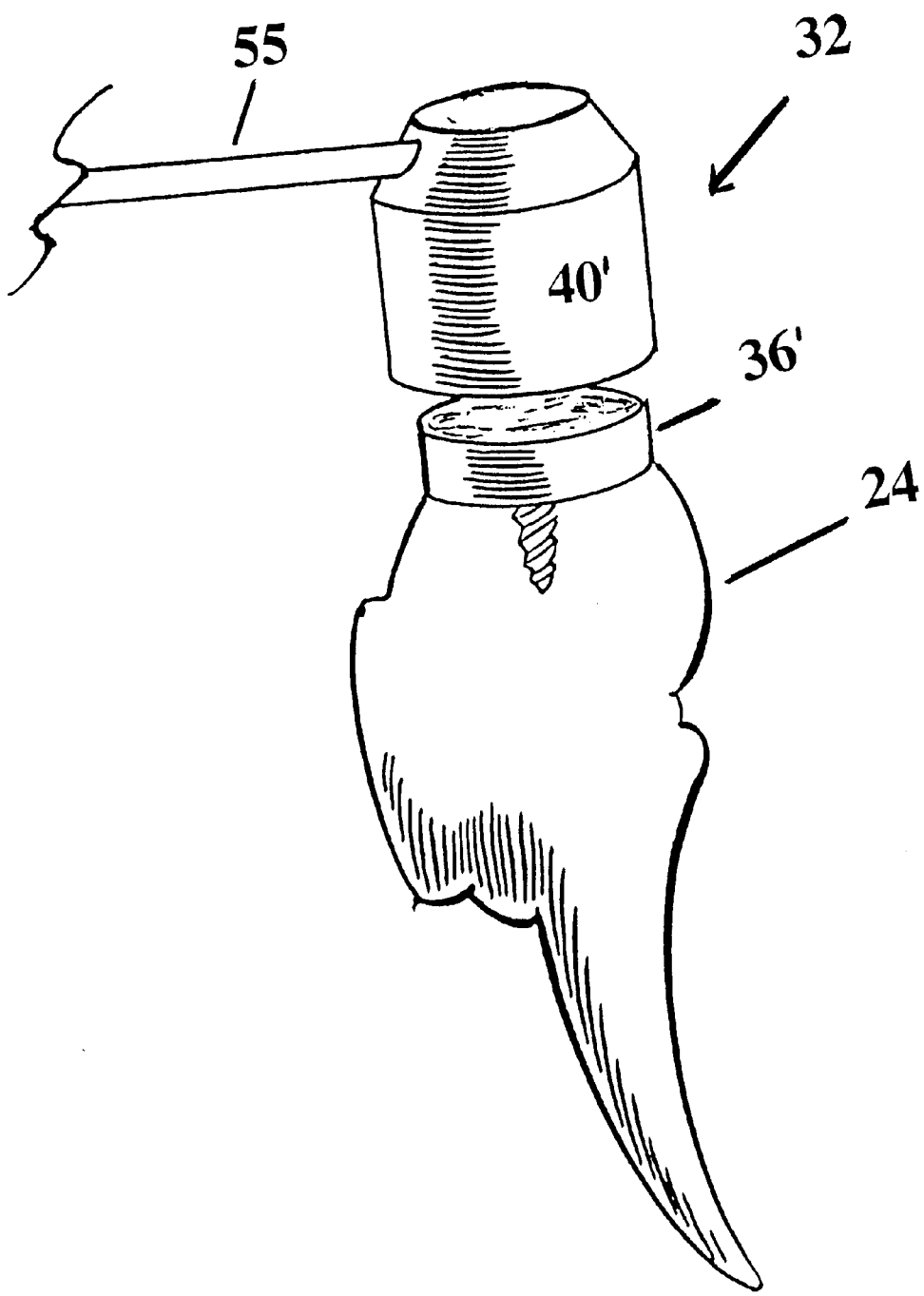
FIG. 4 is an expanded view of the dual coil device as shown in the FIG. 1 depiction.
Figure 5:
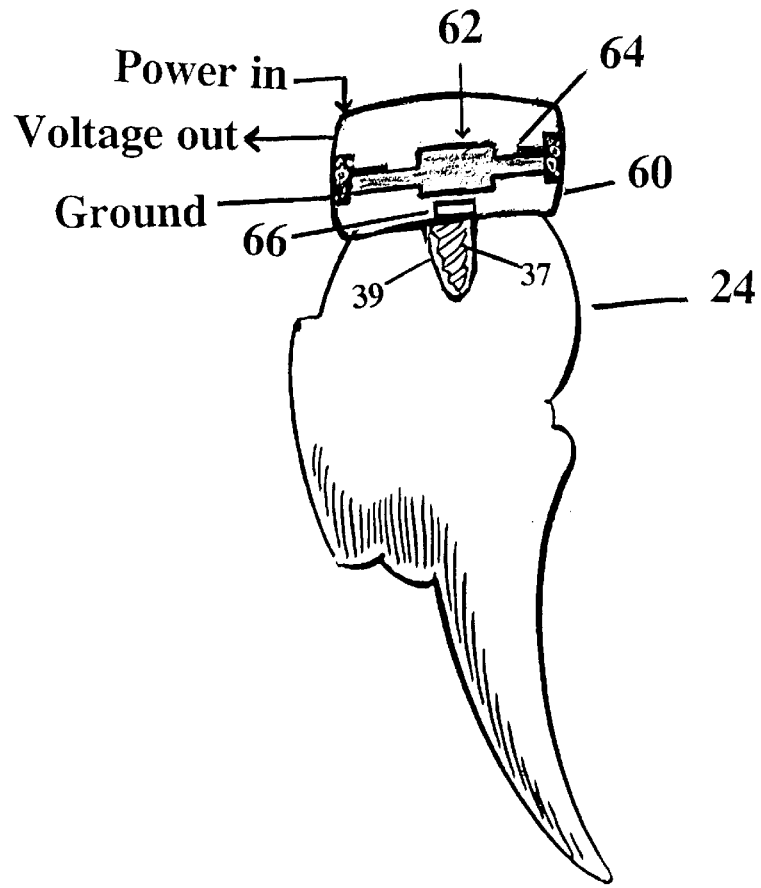
FIG. 5 is an alternate embodiment of the FIG. 4 device using a PZT device.
Figure 6:
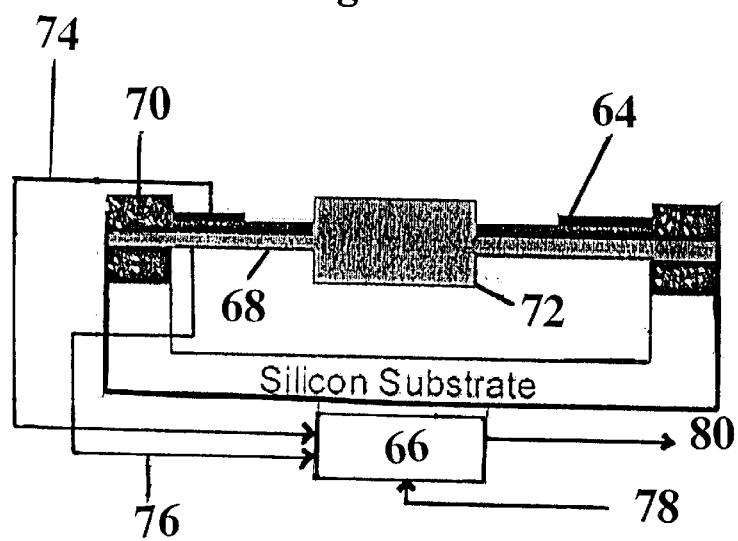
FIG. 6 is an expanded view of the PZT shown in FIG. 5.

Turning next to FIGS. 5–6, an alternate design for the FIG. 4 device is described using a piezoelectric sensor assembly to detect the malleus movements and convert same to an electrical signal. As seen in FIG. 5, a Titanium capsule 60 is attached to the malleus 24 as per the procedure described in reference FIG. 4. Inside the capsule 60 is mounted a piezoelectric assembly 62 comprising a piezoelectric vibration sensor (PZT) 64 and an amplifier 66. The PZT is mounted on a brass sheet 68 connected to the inside walls 70 of the Titanium capsule 60. A brass weight 72 is centrally located on the PZT to impart momentum to the deformable PZT. A voltage signal is transmitted from both sides of the PZT along lines 74, 76 to the amplifier 66 which is powered along line 78 by voltage supplied by the rechargeable battery. In operation, the vibration of the malleus 24 is transmitted to the capsule 60 and the brass sheeting connected thereto is similarly vibrated causing a deformation of the PZT and the establishing of a voltage differential across the sides of the PZT. This voltage differential is amplified by the amplifier 66 which establishes a signal along line 80 indicative of the malleus vibration.

Figure 7:
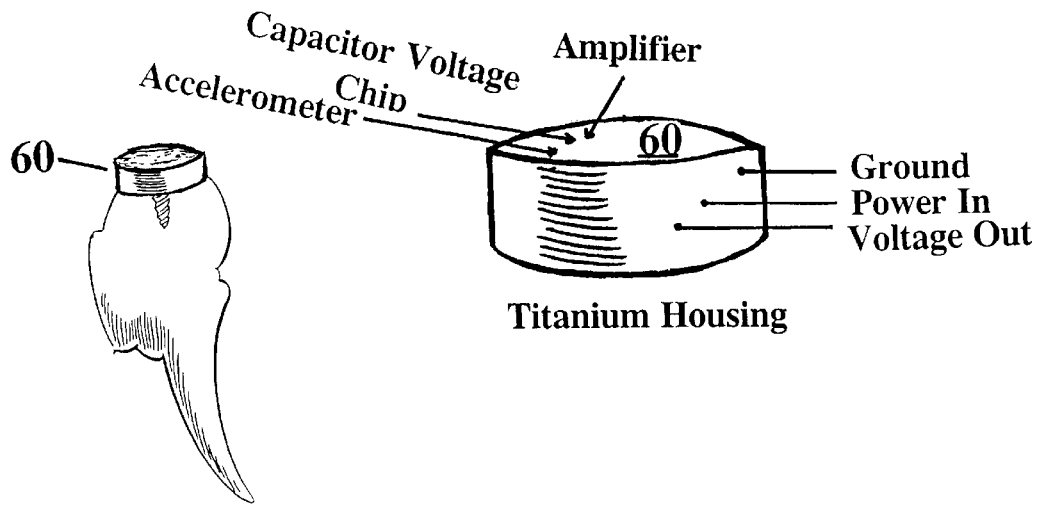
FIG. 7 is an alternate embodiment of the FIG. 3 device using an accelerometer device.
Figure 8:
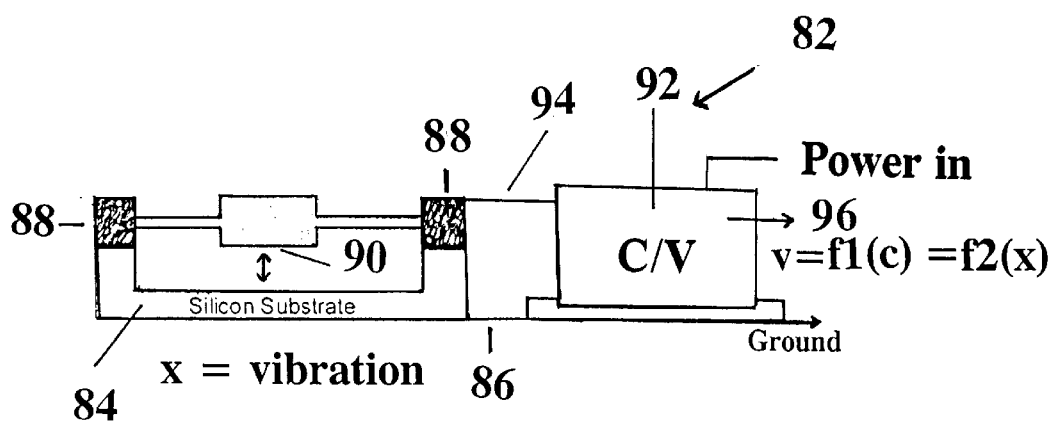
FIG. 8 is an expanded view of the capacitive accelerometer device of FIG. 7 along with the associated capacitor chip.

Turning to FIGS. 7–8 yet another embodiment is disclosed using a capacitive accelerometer assembly 82 mounted inside a titanium sealed capsule 60 as per the FIG. 3 description which is mounted to the malleus also as per the FIG. 3 description. The accelerometer comprises a silicone base 84 affixed to the floor of the capsule 60 to move therewith when the malleus vibrates. The base is grounded through ground wire 86. Spaced from the base and retained between posts 88 is a flexible silicone diaphragm which moves in relation to the base 84 in response to the malleus vibrations to provide a different capacitance defined by c=f(x) or a direct functional relationship between capacitance and the difference in diaphragm spacing between base 84 and diaphragm 90. This capacitance is transmitted to a known capacitance to voltage (C/V) chip 92 along line 94 which outputs a voltage signal proportional to the input capacitance along line 96. The assembly is powered by the implantable rechargeable battery.

Figure 9:
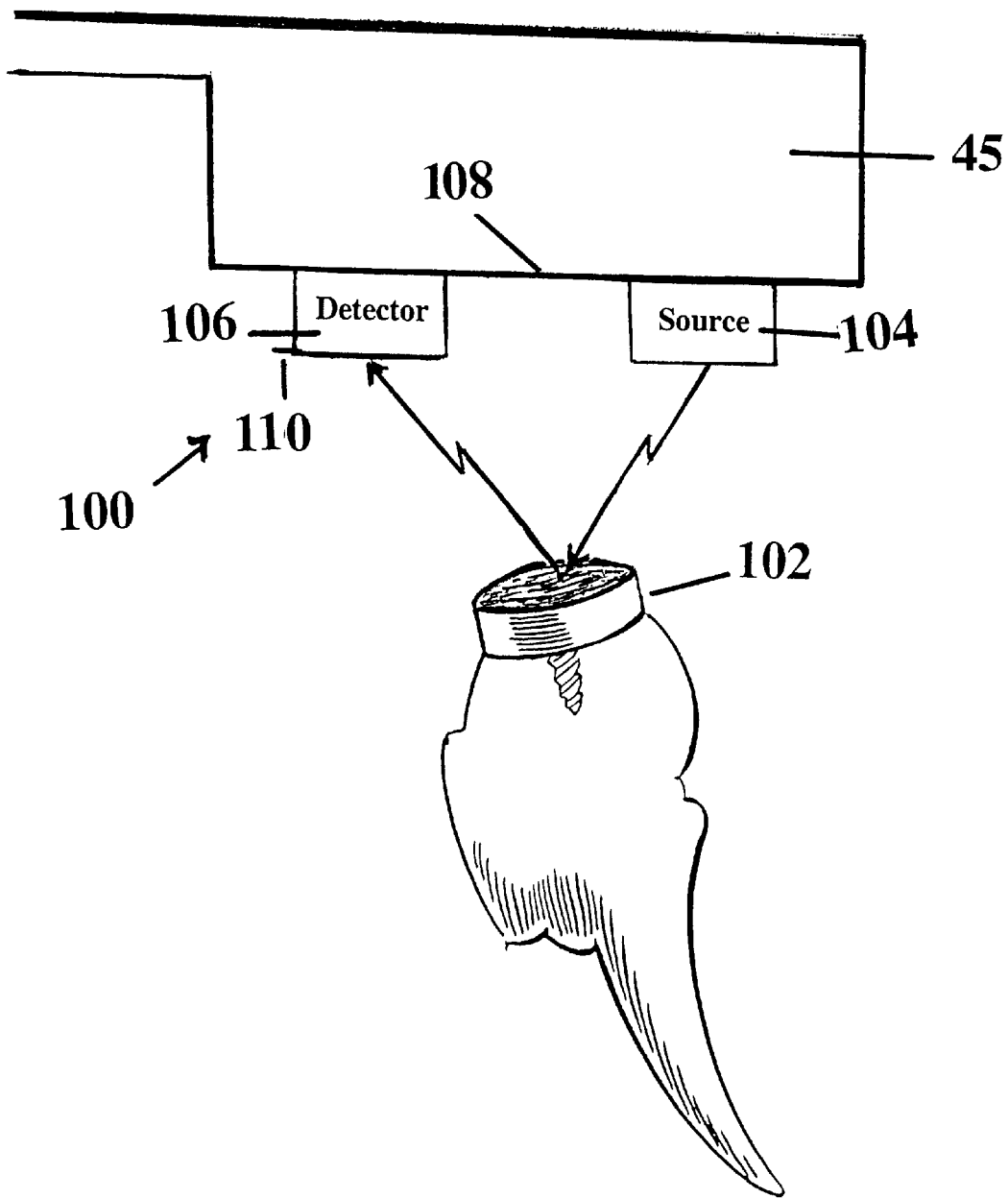
FIG. 9 is a schematic depictions of the optical transducer.

Turning to the fourth embodiment as shown in FIG. 9, an optical transducer assembly 100 is comprised of a reflective surface 102 such as gold, platinum, or polished metal is affixed to the head of the malleus as per the previous descriptions. An optical source 104 such as an LED (light emiting diode is supportably mounted on a plate 108 which is in turn mounted to the adjustable bracket 45. The LED is adjusted to emit light to the surface 102 and be reflected therefrom to known detector assembly 106 for converting light energy to electrical energy. The vibration of the malleus results in a varying reflective light position being located by the detector 106. The detector assembly 106 converts these varying light positions to a varying level electrical output signal along line 110. This electrical signal can be amplified by known amplifier chips and connected to signal processing chips. This is similar to the electrical signals from the previous transducers.

Certain improvements and modifications will be obvious to people of ordinary skill in the art area. It will be understood that they have been deleted herein for the sake of conciseness and readability but are fully intended to be within the scope of the following claims.

What is claimed is:

1. A totally implantable cochlear implant hearing device which is insensitive to MRI interference for improvement of hearing loss comprising:
    a first coil assembly adapted to be mounted on the ossicular chain of a middle ear;
    a second coil assembly;
    means for mounting said second coil assembly a predetermined distance from said first coil assembly in a contactless manner;
    means adapted to be mounted in the middle ear and mastoid cavity for transforming acoustic signal into electrical signals; and
    an electrical assembly located on said mounting means for receiving a said electrical signals from said translating means and sending them to said second coil to actuate same in response thereto.

2. A device as set forth in claim 1 wherein said first coil is a copper driving coil having no ferrite core.

3. A device as set forth in claim 2 wherein said second coil is Titanium.

4. A device as set forth in claim 3 wherein said second coil is sealed in a titanium case which is adapted to be bonded to the malleus of the middle ear.

5. A device as set forth in claim 1 wherein said first coil is a copper driving coil having a ferrite core.

6. An implantable hearing device which is insensitive to MRI interference for improvement of hearing loss comprising:
    a sealed titanium case adapted to be mounted to the ossicular chain; and
    a capacitive variation accelerometer device mounted in said sealed titanium case to respond to the vibrations of the ossicular chain to establish an electrical signal in response to the vibrations of the ossicular chain.

7. A device as set forth in claim 6 including a C/V chip connected to said capacitance variation signal from said accelerometer to convert it into a voltage signal.

8. A device as set forth in claim 7, wherein said sealed titanium case adapted to be mounted to the malleus.

9. An implantable transducer which is insensitive to MRI interference for improvement of hearing loss comprising:
    a light emitting diode adapted to be fixedly mounted to the temporal bone;
    a reflecting surface adapted to be mounted on the malleus; and
    a light detector adapted to be fixedly mounted to the temporal bone to receive the light signals reflected from said reflecting surface and convert same to electrical signals.

* * * * *